United States Patent
Iwata et al.

(10) Patent No.: US 11,904,058 B2
(45) Date of Patent: Feb. 20, 2024

(54) HYDROGEL OBJECT AND METHOD OF MANUFACTURING HYDROGEL OBJECT

(71) Applicant: RICOH COMPANY, LTD., Tokyo (JP)

(72) Inventors: Hiroshi Iwata, Kanagawa (JP);
Tatsuya Niimi, Kanagawa (JP);
Yoshihiro Norikane, Kanagawa (JP);
Takashi Matsumura, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 1209 days.

(21) Appl. No.: 16/557,570

(22) Filed: Aug. 30, 2019

(65) Prior Publication Data
US 2019/0381784 A1    Dec. 19, 2019

Related U.S. Application Data

(63) Continuation of application No. 15/209,268, filed on Jul. 13, 2016, now Pat. No. 10,442,181.

(30) Foreign Application Priority Data

Jul. 22, 2015  (JP) .................................. 2015-144653
Jul. 22, 2015  (JP) .................................. 2015-144803
Jul. 22, 2015  (JP) .................................. 2015-145162

(51) Int. Cl.
| | |
|---|---|
| *A61L 15/60* | (2006.01) |
| *B33Y 70/00* | (2020.01) |
| *C08K 5/05* | (2006.01) |
| *B29C 64/112* | (2017.01) |
| *C08K 5/053* | (2006.01) |
| *B33Y 80/00* | (2015.01) |
| *G09B 23/30* | (2006.01) |
| *B33Y 10/00* | (2015.01) |
| *B29L 31/00* | (2006.01) |
| *B29C 64/40* | (2017.01) |

(52) U.S. Cl.
CPC ............ *A61L 15/60* (2013.01); *B29C 64/112* (2017.08); *B33Y 70/00* (2014.12); *B33Y 80/00* (2014.12); *C08K 5/05* (2013.01); *C08K 5/053* (2013.01); *G09B 23/30* (2013.01); *B29C 64/40* (2017.08); *B29L 2031/7532* (2013.01); *B33Y 10/00* (2014.12)

(58) Field of Classification Search
CPC ............ A61L 15/60; C08K 5/05; G09B 23/30
See application file for complete search history.

(56) References Cited

U.S. PATENT DOCUMENTS

| | | | |
|---|---|---|---|
| 4,305,961 | A | 12/1981 | Tsutsumi et al. |
| 7,780,897 | B2 | 8/2010 | Wicker et al. |
| 2003/0207959 | A1 | 11/2003 | Napadensky et al. |
| 2005/0043696 | A1 | 2/2005 | Schmidt et al. |
| 2005/0249790 | A1 | 11/2005 | Weidl et al. |
| 2007/0255195 | A1 | 11/2007 | Adachi |
| 2011/0182990 | A1 | 7/2011 | Su et al. |
| 2012/0309623 | A1 | 12/2012 | Ahn et al. |
| 2013/0303665 | A1 | 11/2013 | Li et al. |
| 2014/0219973 | A1 | 8/2014 | Boyes et al. |
| 2016/0115297 | A1 | 4/2016 | Norikane et al. |

FOREIGN PATENT DOCUMENTS

| | | |
|---|---|---|
| JP | 55-45665 | 3/1980 |
| JP | 2002-053629 | 2/2002 |
| JP | 2002-128919 | 5/2002 |
| JP | 2004-91755 | 3/2004 |
| JP | 2005-000182 | 1/2005 |
| JP | 2006-028446 | 2/2006 |
| JP | 2006-51182 | 2/2006 |
| JP | 2008-241988 | 10/2008 |
| JP | 2011-076035 | 4/2011 |
| JP | 2013-15789 | 1/2013 |
| JP | 2013-517353 | 5/2013 |
| JP | 2013-194084 | 9/2013 |
| JP | 2013-544929 | 12/2013 |
| JP | 2015-003973 | 1/2015 |
| JP | 2015-108130 | 6/2015 |
| JP | 2015-136895 | 7/2015 |
| JP | 2015-138192 | 7/2015 |
| WO | WO 2011/074188 | 6/2011 |
| WO | WO 2014/065134 | 5/2014 |

OTHER PUBLICATIONS

U.S. Appl. No. 15/066,768, filed Mar. 10, 2016.
Office Action in corresponding Japanese Application No. 2015-144803.
Office Action in corresponding Japanese Application No. 2015-145162.
Office Action in corresponding Japanese Application No. 2015-144653.
Image Information, Published Nov. 1, 2013, vol. 45, No. 11, Issue No. 837 ISSN 1346-1362. (w/Partial Translation).
Industrial 3D Printers: Latest Technology, Materials, and Application Examples, Published May 22, 2015. (w/Partial Translation).

*Primary Examiner* — Angela C Scott
(74) *Attorney, Agent, or Firm* — Grüneberg and Myers PLLC

(57) ABSTRACT

A hydrogel object includes a polymer and water, wherein the rate of mass loss is not greater than 20 percent by mass when the hydrogel object is left undone for one week at 25 degrees C. and relative humidity of 50 percent.

13 Claims, 1 Drawing Sheet

HYDROGEL OBJECT AND METHOD OF MANUFACTURING HYDROGEL OBJECT

CROSS-REFERENCE TO RELATED APPLICATIONS

Figure 1:
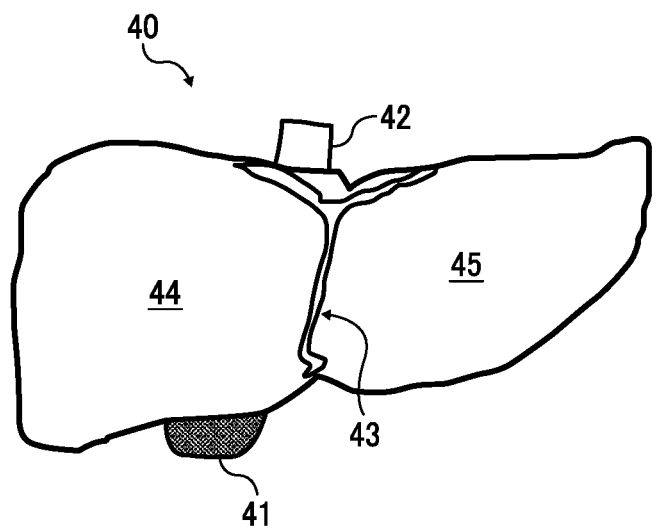

This patent application is based on and claims priority pursuant to 35 U.S.C. § 119 to Japanese Patent Application Nos. 2015-144803, 2015-144653, and 2015-145162, filed on Jul. 22, 2015, Jul. 22, 2015, and Jul. 22, 2015, respectively, in the Japan Patent Office, the entire disclosures of which are hereby incorporated by reference herein.

BACKGROUND

Technical Field

The present invention relates to a hydrogel object and a method of manufacturing the hydeogel object.

Description of the Related Art

Internal organ models manufactured of silicone, urethane elastomer, styrene elastomer, etc. have been developed for procedures for surgical operations.

For a patient to recover from a surgical operation and improve quality of life (QOL), it is demanded for surgeons and assistants thereto to improve their procedure levels to a certain degree. For this reason, internal organ models closer to real human internal organs are required having textures and usability of surgical devices such as an ultrasonic knife and an electrosurgical knife. However, models widely used currently have textures, usability and internal structures far from real internal organs.

Therefore, laboratory animal study using miniature pigs referred to as wet lab is provided as chances for staff who need surgical training using internal organs closer to real. However, human internal organs are different from those of miniature pigs of wet lab in some ways. In addition, it is difficult to provide miniature pigs having appropriate malady for practice. Furthermore, it is extremely expensive to provide an environment for growing miniature pigs fresh while maintaining and controlling their conditions. Therefore, in reality, wet labs for practice are not frequently held.

As a consequence, internal organs true to life are most wanted to improve procedures of surgeons regarding textures and bites of knives in addition to forms of the internal organ.

If such an internal organ model true to life of a patient is prepared before his operation, staff in charge of the patient are able to actually cut or suture the model as a simulation when making a plan of a surgical operation. This contributes to improvement on the chance of success for difficult operations such as enucleation of a tumor.

In addition, materials containing polyvinyl alcohol as the main component are proposed for an internal organ model to reproduce the texture of a real internal organ.

In addition, a hydrogel containing water in a three-dimensional network structure is known. Since this gel has relatively good mechanical properties, it is expected to be applicable to a soft material and an additive manufacturing object including an internal organ model.

SUMMARY

According to the present invention, provided is an improved hydrogel object which includes a polymer and water, wherein the rate of mass loss is not greater than 20 percent by mass when the hydrogel object is left undone for one week at 25 degrees C. and relative humidity of 50 percent.

BRIEF DESCRIPTION OF THE VIEW OF THE DRAWING

Figure 2:
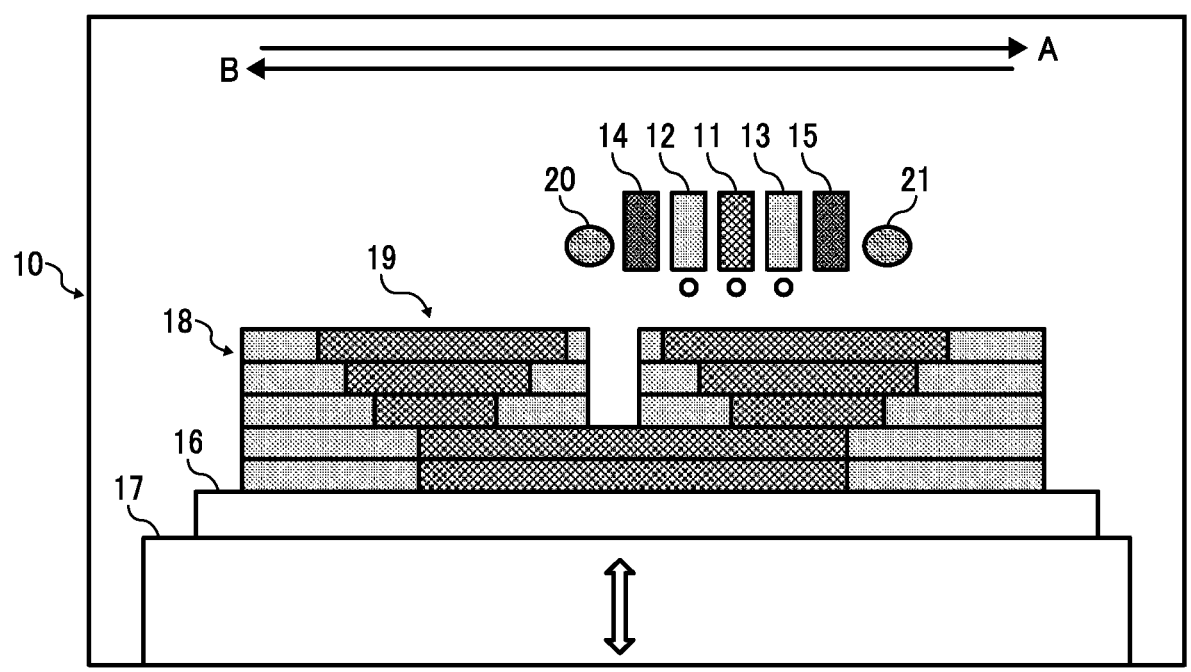

Various other objects, features and attendant advantages of the present invention will be more fully appreciated as the same becomes better understood from the detailed description when considered in connection with the accompanying drawings in which like reference characters designate like corresponding parts throughout and wherein:

FIG. 1 is a schematic diagram illustrating an example of an internal organ model (liver), which is a typical example of a three-dimensional object; and FIG. 2 is a schematic diagram illustrating an example of a 3D printer to manufacture a hydrogel object (three-dimensional object) according to an embodiment of the present invention.

The drawing is a diagram illustrating an example of the image forming apparatus according to an embodiment of the present invention.

DESCRIPTION OF THE EMBODIMENTS

According to the present disclosure, a hydrogel object (three-dimensional object) having good storage stability is provided.

Also, according to the present disclosure, a hydrogel object (three-dimensional object) is provided which truly reproduces internal structures such as vessels and malady, has textures and bites by a knife extremely close to those of a target internal organ, and can be dissected by a surgical scalpel.

The hydrogel object (three-dimensional object) of the present disclosure has many applications. In particular, the three-dimensional object taking advantage of features of a hydrogel and having a stress under 80 percent compression (80 percent compressive stress-strain) of 0.01-5.0 MPa is suitable as soft material, in particular an internal organ model. In addition, the hydrogel object (three-dimensional object) of the present disclosure can be used as insole of a shoe and a grip for slip prevention. The deficiency of the three-dimensional object is improved while utilizing the characteristics of a hydrogel.

Soft material, more specifically, internal organ model as an application example, is described below.

Internal Organ Model

The internal organ model includes a hydrogel including a polymer, water, and preferably a mineral. The mineral is preferably a complexed laminate clay mineral. Storage stability of the internal organ model is improved according to the method described below.

The method of preparing a hydrogel structure containing a humectant in an amount of 10-90 percent by mass or the method of providing a film having moisturizing property to the outer circumference of the surface of the hygrogel structure is suitable.

As a result, the rate of mass loss of the hydrogel object is not greater than 20 percent by mass when the hydrogel object is left undone for one week at 25 degrees C. and relative humidity of 50 percent. It is also possible to decrease the rate of mass loss to not greater than 5 percent by mass.

The internal organ model includes a polymer and optionally a mineral to sustain mechanical strength and have elasticity equivalent to those of a real internal organ. The internal organ model can be manufactured by using a polymerizable monomer and a hydrogel liquid precursor including the mineral.

The internal organ model includes a hydrogel in which a polymer and a mineral is complexed.

In this case, the content ratio between the polymer and the mineral is changed to truly reproduce internal organ information such as suitable hardness and viscoelasticity. That is, an organic-inorganic complex hydrogel enclosing water is included in the three-dimensional network structure of the polymer and the mineral so that the mechanical strength is maintained and elasticity equivalent to a real internal organ is obtained. In addition, the organic-inorganic complex hygrogel having the structure described above has good distensibility. Furthermore, such a model has the same texture as that of a real internal organ and the bite of a surgical scalpel is extremely close to that for the real internal organ.

In addition, since the internal organ model contains water in the hydrogel, storage stability causes a slight problem. For example, when an internal organ contracts with progress of drying, internal organ information such as form, suitable hardness, and viscoelasticity are not truly reproduced, wetting texture of the surface is lost, and transparency is degraded by propagation of germs such as fungus.

Hydrogel Liquid Precursor

The hydrogel liquid precursor includes, for example, a polymerizable monomer and a laminate clay mineral dispersible in water, and preferably water and a humectant accounts for 10-90 percent by mass.

In addition, optionally a film having moisturizing property is provided to the outer circumference of the surface of the hygrogel structure.

Moreover, it is preferable to include a preservative accounting for 25 percent by mass or less.

Polymer

There is no specific limit to the polymer and a suitable polymer is selected to suit to a particular application. For example, a water-soluble polymers are preferable because a hydrogel is hydrous.

As the water-soluble polymer, polymers having, for example, an amide group, an amino group, a hydroxyl group, a tetramethyl ammonium group, a silanol group, an epoxy group, etc. are suitable.

The water-soluble polymer is suitable to maintain the strength of an aqueous gel.

The polymer can be a homopolymer (monopolymer) and heteropolymers (copolymers). These can be modified. Known functional groups can be introduced into these. Forms of salts are also allowed.

Water-solubility of the water-soluble polymer for use in the present disclosure is that, for example, when 1 g of the water-soluble polymer is mixed with and stirred in 100 g of water at 30 degrees C., 90 percent by mass or more of the polymer is dissolved in water.

As the polymerizable monomer polymerized to obtain the water-soluble polymer, for example, acrylamide, N-substituted acrylamide derivative, N,N-di-substituted acrylamide derivative, N-substituted methacrylamide derivative, and N,N-di-substituted methacrylamide derivative. These can be used alone or in combination.

Specific examples of the polymerizable monomer include, but are not limited to, acrylamide, N,N-dimethylacrylamide, and N-isopropylacrylamide.

The proportion of the polymerizable monomer is not particularly limited and can be suitably selected to suit to a particular application. For example, it is preferably 0.5-20 percent by mass to the total content of the hydrogel liquid precursor.

Mineral

There is no specific limitation to the mineral and it can be suitably selected to suit to a particular application. For example, a laminate clay mineral is preferable. In addition, since a hydrogel is hydrous, water swellable clay mineral is preferable which is uniformly dispersible in water at the level of primary crystal.

Examples of such water swellable clay mineral are water swellable smectite and water swellable mica.

Specific examples thereof include, but are not limited to, water swellable hectorite containing sodium as an interlayer ion, water swellable montmorillonite, water swellable saponite, and water swellable synthesized mica.

The water swellable clay mineral mentioned above can be used alone or in combination. In addition, it is suitable to synthesize such a mineral and also use products available on the market.

Specific examples of the product available on the market include, but are not limited to, synthesized hectorite (laponite XLG, manufactured by RockWood), SWN (manufactured by Coop Chemical Ltd.), and fluorinated hectorite SWF (manufactured Coop Chemical Ltd.).

The proportion of the water swellable clay mineral is not particularly limited and can be suitably selected to suit to a particular application. For example, it is preferably 1-40 percent by mass to the total content of the hydrogel liquid precursor.

Water

As the water, deionized water, ultrafiltered water, reverse osmosis water, pure water such as distilled water, and ultra pure water can be used.

It is suitable to dissolve or disperse other components such as organic solvents in the water to impart antibiotic property, or electroconductive property, and adjust hardness.

Humectant

Specific examples of the humectant include, but are not limited to, alkyl alcohols having one to four carbon atoms such as methylalcohol, ethyl alcohol, n-propyl alcohol, isopropyl alcohol, n-butyl alcohol, sec-butyl alcohol, and tert-butyl alcohol, amides such as dimethylfornamide and dimethylacetoamide, ketones or ketone alcohols such as acetone, methylethylketone, and diacetone alcohol, ethers such as tetrahydrofuran and dioxane, multi-valent polyols such as ethylene glycol, propylene glycol, 1,2-propane diol, 1,2-butane diol, 1,3-butane diol, 1,4-butane diol, diethylene glycol, triethylene glycol, 1,2,6-hexane triol, thioglycol, hexylene glycol, and glycerin, polyalkylene glycols such as polyethylene glycol and polypropylene glycol, lower alcohol ethers of polyols such as ethylene glycol monomethyl (or ethyl) ether, diethylene glycol methyl (or ethyl) ether, and triethylene glycol monomethyl (or ethyl) ether, alkanol amines such as monoethanol amine, diethanol amine, and triethanol amine, N-methyl-2-pyrolidone, 2-pyrolidone, 1,3-dimethyl-2-imidazoline. These can be used alone or in combination. Of these, in terms of moisture retention, polyols are preferable and glycerin is more preferable.

The suitable proportion of the humectant is 10-50 percent by mass to the hydrogel liquid precursor. When the proportion is not greater than 10 percent by mass, drying is not easily prevented. When the proportion is not less than 50 percent by mass, a laminate clay mineral may not be uniformly dispersed.

To impart the moisturizing feature, it is suitable to contain a humectant in the hydrogel liquid precursor. This is deferred in detail.

Preservative

The preservative prevents generation and growing of microbes, in particular germs and fungus. It is preferable that the preservative be dissolvable or stably dispersible in water, practically sufficiently antibiotic, antiseptic, safe, and less burden on environment.

The preservative includes organic preservatives and inorganic preservatives. For example, specific compounds are mentioned in, for example, Handbook of Antibacterial and Antifungal, Res. Soc. for Antibacterial and Antifungal Agents Japan, GIHODO SHUPPAN Co., Ltd., 1986 and Encyclopedia of Antibacterial and Antifungal, Res. Soc. for Antibacterial and Antifungal Agents Japan.

Examples of the organic preservative are nitrogen-containing heterocyclic compounds, quaternary ammonium salts, phenolic compounds, alcohol compounds, carboxylic acid compounds, and other organic preservatives. Of these, nitrogen-containing heterocyclic compounds are preferable.

Examples of the nitrogen-containing heterocyclic compounds are pyridine compounds, pyrimidine compounds, pyrazole compounds, oxazole compounds, oxazine compounds, imidazole compounds, benzimidazoloe compounds, diadine compounds, 1,3,5-triadine compounds, hexahydrotriadine compounds, triazole compounds, isooxazole compounds, thiazole compounds, thiadiadine compounds, benzthiazole compounds, thiazolin-2-one compounds, isothiazoline-3-one compounds, benzoisothiazolin-3-one compounds, benzothiazoline-2-one compounds, tetrahydrothiadiadine-2-thione compounds, morpholine compounds, and pyrrole compounds.

Specific examples of the nitrogen-containing heterocyclic compound include, but are not limited to, thiabendazole, 2-benzisothiazoline-3-one, 1,2-benzisothiazolo-3(2H)-one, 1,2-benzoisothiazoline-3-one, 3,4-isothiazoline-3-one, benzoisothiazolone, alkylisothiazolone, chloroalkyl isothiazolone, benzisothiazolone, benzimidazole, thiabendazole, thiazosulfamide, pyridine thioloxide, 2-mercaptobenzothiazole, 2-(4-thiazoyl)-benzoimidazole, 2-methoxy-carbonyl aminobenzoimidazole, sodium pyridine thion-1-oxide, and 4,4-dimethyloxazolidine.

Specific examples of the quaternary ammonium salt include, but are not limited to, tetrabutyl ammonium chloride, cetyl pyridinium chloride, benzyltrimethyl ammonium chloride, benzalconium chloride, alkyltrimethyl ammonium chloride, cetylpyridinium chloride, and benzetonium chloride.

Specific examples of the phenol compounds include, but are not limited to, phenol, thimol, chlorophenol, dichlorophen, hexachlorophene, bromophenol, chlorobromophenol, crezol, guaiacol, o-phenylphenol, xylenol, chloroxylenol, phenol sulphonic acid, resorcin, pyrogallol, phenoxyethanol, and bisphenol.

Specific examples of alcohol include, but are not limited to, ethanol, chlorbutanol, isopropanol phenoxy alcohol, aralkyl alcohol, and phenoxy ether.

Specific examples of carboxulic acid compounds include, but are not limited to, benzoic acid, sodium benzoate, monobromo acetic acid ester, p-hydroxy benzoic acid ester, sorbic acid, sodium sorbate, potassium sorbate, calcium sorbate, and sorbic acid esters.

Specific examples of the organic preservative include, but are not limited to, bromo-based preservatives ($CH_3CONHBr$, $C_6H_5$—$CH_2OCOCH_2Br$, $HOH_2C$—$CBr(NO_2)$—$CH_2OH$, etc.), amines (hexamethylene tetramine, alkylguanidein, nitromethylbenzyl ethylene diamine, etc.), acid amides, carbamic acid, carbamates, thioureas, thiosemicarbazides, dithiocarbamates, sulfides, disulfides, sulphoxides, sulfamides, and organic mercury compounds (phenyl acetic acid mercury, phenyl oleic acid mercury, etc.).

Specific examples of inorganic preservatives include, but are not limited to, inorganic materials including heavy metal ions such as silver ion or salts thereof.

The preservative can be used alone or in combination. Various preservatives such as oil-soluble preservatives and water-soluble preservatives can be used. Water-soluble preservatives are preferable.

Of these, the nitrogen-containing heterocyclic compound and butylcarbamic acid ionized propynyl are preferable. Thiabendazole, 2-benzisothiazoline-3-one, 1,2-benzisothiazolo-3(2H)-one, 1,2-benzoisothiazoline-3-one, 3,4-isothiazoline-3-one, benzoisothiazolone, alkylisothiazolone, chloroalkylisothiazolone, benzisothiazolone, benzimidazole, thiabendazole, thiazosulfamide, pyridine thioloxide, butylcarbamic acid ionized propynyl, and N-n-butyl-1,2-benzoisothiazoline-3-one are more preferable. 2-benzisothiazoline-3-one, 1,2-benzisothiazolo-3(2H)-one, 1,2-benzoisothiazoline-3-one, 3,4-isothiazoline-3-one, butylcarbamic acid ionized propynyl, and N-n-butyl-1,2-benzoisothiazoline-3-one are furthermore preferable. 1,2-benzoisothiazoline-3-one is particularly preferable.

Specific examples of the product of the preservative available on the market include, but are not limited to, Proxel CRL, Proxel BDN, Proxel LV, Proxel GXL(S), Proxel XL2, Proxel IB, Proxel TN, Glycacil 2000, and DENSIL DN (all manufactured by LONZA Japan).

The proportion of the preservative is preferably not greater than 25 percent by mass, more preferably 0.01-10 percent by mass, and furthermore preferably 0.05-5 percent by mass to the total content of hygrogel. When the proportion is not greater than 25 percent by mass, storage stability of an obtained three-dimensional object is improved without growing of germs such as fungus and reaction inhibition caused by adsorption of the preservative to a laminate mineral can be prevented. As a result, the obtained three-dimensional object has good transparency and electric conductivity.

The content of the preservative can be measured by using, for example, thermogravimetric analyzer (Thermo plus TG8120, manufactured by Rigaku Corporation).

To measure the content of the preservative of the surface of the three-dimensional object, a hydrogel having a size of 2 mm×2 mm is cut out from the surface of the three-dimensional object first. This hydrogel is placed in a thermogravimetric analyzer to measure the thermogravimetric decrease rate around the boiling point of the preservative. To be specific, when Proxel GXL(S) (manufactured by LONZA Japan) is used, since Proxel GXL(S) contains 1,2-benzoisothiazoline-3-one having a boiling point of 154-158 degrees C. in an amount of 20 percent by mass, the mass loss rate of 1,2-benzoisothiazoline-3-one is measured in the temperature range of 120-160 degrees C. The proportion of the preservative can be calculated from the mass loss ratio rate of 1,2-benzoisothiazoline-3-one when the mass of the 2 mm×2 mm hydrogel is determined to be 100 percent.

The content of the preservative in the center portion of the three-dimensional object is obtained by cutting out a hydrogel of 2 mm×2 mm at 50 mm inside from the surface of the three-dimensional object and measuring the decrease ratio in the same manner as in the case of the surface.

Moisturized Film

There is no specific limitation to form the moisturized film and it can be suitably selected to suit to a particular application. For example, a three-dimensional object model is dipped in 0.01 percent by mass aqueous solution of highly moisturized polysaccharide (Tremoist-TP, manufactured by MATSUMOTO TRADING Co., Ltd.) for 30 minutes at 40 degrees C. and dried to form a thin film. A method including applying a non-volatile component such as oil to the surface of a three-dimensional object model is also suitable.

Film Forming

The film is formed on the surface of a hygrogel structure to achieve the following 1-3.
1. To maintain the form of the hygrogel structure
2. To improve storage property (dry hardiness, asepticus) of a three-dimensional object model
3. To improve the appearance of the hygrogel structure.

To maintain the form of a hygrogel structure, it is preferable to have an elastic film to prevent collapse due to the mass of the structure itself. It is preferable that the difference of Young's modulus between a three-dimensional object with a film and no film be not less than 0.01 MPa. Specific example of the material to form a film include, but are not limited to, polyester, polyolefin, polyethylene terephthalate, PPS, polypropylene, PVA, polyethylene, polyvinyl chloride, cellophane, acetate, polystyrene, polycarbonate, nylon, polyimide, fluororesins, and paraffin wax.

In addition, as the film thickness decreases, the texture of a three-dimensional object is kept better, so that the film preferably has a thickness of not greater than 200 μm.

To improve storage property, dry hardiness and asepticus have to be improved. To improve dry hardiness, water vapor transmission rate (JIS K7129) of a film is preferably not greater than 500 g/m$^2$ and oxygen transmission rate (JIS Z1702) thereof is preferably not greater than 100,000 cc/m$^2$/hr/atm.

To improve asepticus, it is suitable to mix the preservative mentioned above with the film.

Such a film is formed on the surface of a hygrogel structure to improve appearance of the hygrogel structure.

For example, if a scar or roughness is present on the surface of a hydrogel structure, a film is suitable to compensate the appearance. In addition, since the film serves as a sacrifice layer of the surface, the inside of the hygrogel structure can be protected. In addition, although it is not possible to draw a marking on the surface of a hygrogel structure, such a procedure marking can be drawn on the film formed on the surface for a simulation before an operation. Therefore, film forming contributes to improving function as the model.

There is no specific limit to the method of forming a film as long as it improves the functionality mentioned above. For example, following methods are suitable.

For example, it is suitable to dissolve the material for forming a film mentioned above in a solvent and applying the solution to the surface of a hydrogel structure. As the application method, for example, the liquid can be applied by a brush or sprayed by a spray, or a hydrogel structure can be impregnated with the liquid.

In addition, a heat contraction film is used as the material for forming a film to form a laminate on the surface of a hygrogel structure.

Moreover, it is also suitable to dissolve the material for forming a film in a solvent and form a film of the solution at the same time when manufacturing a hygrogel structure by a three-dimensional printer.

Other Components

The hydrogel liquid precursor may include other optional components such as a coloring material, a fragrance, and an antioxidant.

If a coloring material is used, it is possible to color an internal organ model close to the color of a human internal organ.

It is preferable that an inclusion (internal structure) having different color or hardness be disposed at a target position in the internal organ model. For this reason, the position to put a surgical knife into can be confirmed before an operation.

The inclusion includes, for example, mimickers such as vessels, tubes, and malady, cavity, and cockle.

The hardness can be adjusted, for example, by changing the content of a water swellable laminate clay mineral contained in the hydrogel liquid precursor.

The color can be adjusted, for example, by adding a coloring material to the hydrogel liquid precursor.

There is no specific limitation to the coloring material and it can be suitably selected to suit to a particular application. For example, dyes and pigments are suitable.

Examples of the dye are as follows.

Specific examples of the black dyes include, but are not limited to, MS BLACK VPC (manufactured by Mitsui Chemicals, Incorporated), AIZEN SOT BLACK-1 and AIZEN SOT BLACK-5 (Both manufactured by HODOGAYA CHEMICAL CO., LTD.), RESOLIN BLACK GSN 200% and RESOPIN BLACK BS (both manufactured by Bayer Holding Ltd.), KAYASET BLACK A-N (manufactured by Nippon Kayaku Co., Ltd., DAIWA BLACK MSC (manufactured by Daiwa Fine Chemicals Co., Ltd.), HSB-202 (manufactured by Mitsubishi Chemical Corporation), NEPTUNE BLACK X60 and NEOPEN BLACK X58 (Manufactured by BASF), Oleousoul Fast BLACK RL (manufactured by Taoka Chemical Co., Ltd., Chuo BLACK80 and Chuo BLACK80-15 (manufactured by Chuo synthetic Chemical Co., Ltd.).

Specific examples of the magenta dye include, but are not limited to, MS Magenta VP, MS Magenta HM-1450, and MS Magenta Hso-147 (All manufactured by Mitsui Chemicals, Incorporated), AIZEN SOT Red-1, AIZEN SOT Red-2, AIZEN SOT Red-3, AIZEN SOT Pink-1, SPIRON Red GEHSPECIAL (all manufactured by HODOGAYA CHEMICAL CO., LTD.), RESOLIN Red FB 200%, MACROLEX Red Violet R, MACROLEX ROT 5B (all manufactured by Bayer Holding Ltd.), KAYASET ReD B, KAYASET Red 130, and KAYASET Red 802 (Manufactured by Nippon Kayaku Co., Ltd.), PHLOXIN, ROSE BENGAL, and ACID RED (all manufactured by Daiwa Fine Chemicals Co., Ltd.), HSR-31 AND DIARESIN RedK (both manufactured by Mitsubishi Chemical Corporation), Oil Red (manufactured by BASF), and Oil Pink330 (manufactured by Chuo synthetic Chemical Co., Ltd.).

Specific examples of the cyan dye include, but are not limited to, MS Cyan HM-1238, MS Cyan HSo-16, Cyan Hso-144, and MS Cyan VPG (all manufactured by Mitsui Chemicals, Incorporated), AIZEN SOT Blue-4 (manufactured by HODOGAYA CHEMICAL CO., LTD.), RESOLIN BR.BLUE BGLN 200%, MACROLEX Blue RR, CERES Blue GN, SIRUS SUPRATURQ.Blue Z-BGL, and SIRUS SUPRA TURQ.Blue FB-LL330% (all manufactured by Bayer Holding Ltd.), KAYASET Blue Fr, KAYASET Blue N. KAYASET Blue 814, Turq.Blue GL-5 200, and Light-Blue BGL-5 200 (all manufactured by Nippon Kayaku Co., Ltd.), DAIWA Blue 7000 and Oleosol Fast Blue GL (both manufactured by Daiwa Fine Chemicals Co., Ltd.), DIARESINBLUE P (manufactured by Mitsubishi Chemical Corporation), SUDAN Blue 670, NEOPEN Blue808, and ZAPON Blue 806 (all manufactured by BASF).

Specific examples of the yellow dye include, but are not limited to, MS Yellow HSm-41, Yellow KX-7, and Yellow EX-27 (manufactured by Mitsui Chemicals, Incorporated), AIZEN SOT Yellow-1, AIZEN SOT Yellow-3, and AIZEN SOT Yellow-6 (all manufactured by HODOGAYA CHEMICAL CO., LTD.), MACROLEX Yellow 6G, MACROLEX FLUOR, and Yellow 10 GN (all manufactured by Bayer Holding Ltd.), KAYASET Yellow SF-G, KAYASET Yellow 2G, KAYASET Yellow A-G, and KAYASET Yellow E-G (all manufactured by Nippon Kayaku Co., Ltd.), DAIWA Yellow 330HB (Daiwa Fine Chemicals Co., Ltd.), HSY-68 (Mitsubishi Chemical Corporation), SUDAN Yellow 146 and NEOPEN Yellow 075 (all manufactured by BASF), and Oil Yellow 129 (manufactured by Chuo synthetic Chemical Co., Ltd.).

Examples of the pigments are organic pigments and inorganic pigments. For example, azo pigments (azo lake, insoluble azo pigments, condensed azo pigments, chelate azo pigments, etc.), polycyclic pigments (phthalocyanine pigments, perylene pigments, perinone pigments, anthraquinone pigments, quinacridone pigments, dioxazine pigments, thioindigo pigments, isoindolinone pigments, and quinofuranone pigments) are suitable. Specific examples of the pigment include, but are not limited to, the organic pigments and inorganic pigments referenced by the following number in Color Index.

Red or Magenta Pigments:
Pigment Red 3, 5, 19, 22, 31, 38, 43, 48:1, 48:2, 48:3, 48:4, 48:5, 49:1, 53:1, 57:1, 57:2, 58:4, 63:1, 81, 81:1, 81:2, 81:3, 81:4, 88, 104, 108, 112, 122, 123, 144, 146, 149, 166, 168, 169, 170, 177, 178, 179, 184, 185, 208, 216, 226, 257, Pigment Violet 3, 19, 23, 30, 37, 50, 88, and Pigment Orange 13, 16, 20, and 36.

Blue or Cyan Pigments:
Pigment Blue 1, 15, 15:1, 15:2, 15:3, 15:4, 15:6, 16, 17-1, 22, 27, 28, 29, 36, and 60

Green Pigments:
Pigment Green 7, 26, 36, and 50.

Yellow Pigments:
Pigment Yellow 1, 3, 12, 13, 14, 17, 34, 35, 37, 55, 74, 81, 83, 93, 94, 95, 97, 108, 109, 110, 137, 138, 139, 153, 154, 155, 157, 166, 167, 168, 180, 185, and 193.

Black Pigments:
Pigment Black 7, 26, and 28.

The pigments are available on the market.

Specific examples thereof include, but are not limited to, CHROMOFINE YELLOW 2080, 5900, 5930, AF-1300, 2700L, CHROMOFINE ORANGE 3700L, 6730, CHROMOFINE SCARLET 6750, CHROMOFINE MAGENTA 6880, 6886, 6891N, 6790, and 6887, CHROMOFINE VIOLET RE, CHROMOFINE RED 6820, 6830, CHROMOFINE BLUE HS-3, 5187, 5108, 5197, 5085N, SR-5020, 5026, 5050, 4920, 4827, 4837, 4824, 4933GN-EP, 4940, 4973, 5205, 5208, 5214, 5221, 5000P, CHROMOFINE GREEN 2GN, 2GO, 2G-500D, 5310, 5370, 6830, CHROMOFINE BLACK A-1103, SEIKAFAST Yellow, 10GH, A-3, 2035, 2054, 2200, 2270, 2300, 2400(B), 2500, 2600, ZAY-260, 2700(B), and 2770, SEIKAFAST RED 8040, C405(F), CA120, LR-116, 1531B, 8060R, 1547, ZAW-262, 1537B, GY, 4R-4016, 3820, 3891, ZA-215, SEIKAFAST CARMINE 6B1476T-7, 1483LT, 6840, and 3870, SEIKAFAST BORDEAUX 10B-430, SEIKALIGHT ROSE R40, SEIKALIGHT VIOLET B800, 7805, SEIKAFAST MAROON 460N, SEIKAFAST ORANGE 900, 2900, SEIKALIGHT BLUE C718, A612, cyanine blue 4933M, 4933GN-EP, 4940, 4973 (all manufactured by Dainichiseika Color & Chemicals Mfg. Co., Ltd.), KET Yellow 401, 402, 403, 404, 405, 406, 416, 424, KET Orange 501, KET Red 301, 302, 303, 304, 305, 306, 307, 308, 309, 310, 336, 337, 338, 346, KET Blue 101, 102, 103, 104, 105, 106, 111, 118, 124, KET Green 201 (all manufactured by DIC Corporation), Colortex Yellow 301, 314, 315, 316, P-624, 314, U10GN, U3GN, UNN, UA-414, U263, Finecol Yellow T-13, T-05, Pigment Yellow1705, Colortex Orange 202, Colortex Red101, 103, 115, 116, D3B, P-625, 102, H-1024, 105C, UFN, UCN, UBN, U3BN, URN, UGN, UG276, U456, U457, 105C, USN, Colortex Maroon601, Colortex BrownB610N, Colortex Violet600, Pigment Red 122, Colortex Blue516, 517, 518, 519, A818, P-908, 510, Colortex Green402, 403, Colortex Black 702, U905 (all manufactured by Sanyo Color Works, LTD.), Lionol Yellow 1405G, Lionol Blue FG7330, FG7350, FG7400G, FG7405G, ES, ESP-S (all manufactured by TOYO INK CO., LTD.), Toner Magenta E02, Permanent RubinF6B, Toner Yellow HG, Permanent Yellow GG-02, Hostapeam BlueB2G (all manufactured by Hoechst AG, carbon black #2600, #2400, #2350, #2200, #1000, #990, #980, #970, #960, #950, #850, MCF88, #750, #650, MA600, MA7, MA8, MA11, MA100, MA100R, MA77, #52, #50, #47, #45, #45L, #40, #33, #32, #30, #25, #20, #10, #5, #44, CF9 (all manufactured by Mitsubishi Chemical Corporation).

The proportion of the coloring material is not particularly limited and can be suitably selected to suit to a particular application. For example, it is preferably 0.1-5 percent by mass to the total content of the hydrogel liquid precursor.

Method of Manufacturing Internal Organ Model

There is no specific limitation to the method of manufacturing the hydrogel object of the present disclosure as an internal organ model. It can be suitably selected to suit to a particular application. In general, the internal organ model has to reproduce a complex form based on the original 3D data. Also, since the model has mixed portions of different characteristics, it is preferable to manufacture the internal organ model in the following manner.

For example, it is suitable to manufacture a mold by a suitable processing method and charge a hydrogel liquid precursor into the mold for curing. Inclusions such as vessels are separately formed and can be disposed at a predetermined position in the mold.

When manufacturing the mold and the inclusion such as vessels, it is preferable to subject metal or a resin to cutting, stereolithography, a 3D printer based on 3D data.

In addition, it is possible to laminate a hydrogel liquid precursor and optional support liquid based on 3D data using a manufacturing (forming) device referred to as a 3D printer. To be more specific, it is preferable to discharge a gel liquid precursor by a material jetting forming device employing an inkjet method to form an internal organ model with precision. It is also possible to use a stereolithographic device irradiating a pool storing a gel precursor with light to cure and laminate the gel.

The support liquid is used to manufacture a support at the same time when manufacturing the three-dimensional object by a 3D printer to support and stably form a three-dimensional object. The support is removed after the laminate object is completed. Specific example of the material for a support include, but are not limited to, polyester, polyolefin, polyethylene terephthalate, PPS, polypropylene, PVA, polyethylene, polyvinyl chloride, cellophane, acetate, polystyrene, polycarbonate, nylon, polyimide, fluororesins, paraffin wax, acrylic resins, and epoxy resins.

The method of manufacturing a three-dimensional object having multiple areas where compression stress values are different is described below.

Multiple liquid precursors having different compositions are used as the hygrogel precursor. In the first process, a film having multiple areas where post-curing compression stress values or post-curing modulus of elasticity values are different is formed by controlling the imparting position and the imparting amount of the multiple liquid precursors.

By repeating this film forming, a laminate object having multiple areas having different compression stress values can be obtained.

Specifically, for example, a liquid precursor A and a liquid precursor B having different composition from the liquid precursor A are prepared. For example, three-dimensional compression stress distribution data are obtained by using MR Elastography (MRE) and thereafter input into a three-dimensional object manufacturing device. Based on the input compression stress data, the mixing ratio of the liquid precursor A and the liquid precursor B to be discharged to positions corresponding to the data of three-dimensional form is determined. The liquid precursor A and the liquid precursor B are discharged to the determined area in the determined mixing ratio to form a dot. This is repeated to form a liquid film and this film-forming is repeated to obtain a three-dimensional object having multiple areas having different compression stress values.

Storage stability of the hydrogel object (three-dimensional object) of the present disclosure is secured by a humectant contained therein.

The method of causing the three-dimensional object to contain a humectant include, for example, the following 1 and 2.

Method 1 of obtaining a three-dimensional object using a hydrogel liquid precursor containing a humectant.

Method 2 of obtaining a three-dimensional object using a hydrogel liquid precursor including no humectant and thereafter post-treating the three-dimensional object with liquid including a humectant.

According to the method 1, the humectant is contained in all over the three-dimensional object.

If the method 2 is employed, the humectant is contained around the surface of the three-dimensional object.

The method 1 is a simple method having a less number of processes because a hydrogel liquid precursor including a humectant is cured to obtain a three-dimensional object containing the humectant. However, according to this method, if a humectant is mixed with a hydrogel liquid precursor and accounts for more than 50 percent by mass, the laminate clay mineral is not uniformly dispersed. Therefore, curability of the hydrogel may be inhibited depending on the kind of humectant. Therefore, it is preferable that the mixing ratio of a humectant with a hydrogel liquid precursor be 10-50 percent by mass.

In the method 2, for example, an object is formed by a mold or a 3D printer using a hydrogel liquid precursor containing no humectant and thereafter the object is treated with liquid containing a humectant. More specifically, the object is immersed in liquid containing a humectant (solvent or additive can be optionally added). According to this treatment, the humectant can be impregnated into the object from the surface toward the bulk direction. The density and the dipping (immersing) time of a humectant can be adjusted depending on the state of a hygrogel.

In this method, a three-dimensional object is post-treated with liquid containing a humectant after a hydrogel is cured so that curability of the hydrogel is not inhibited.

If the method 2 is employed, a laminate object can be manufactured in which density of the humectant is high around the surface and low inside. Also the obtained three-dimensional object maintains good transparency and electric conductivity.

Also, in the method 2, it is possible that a three-dimensional object is dried by using a humectant containing no humectant to evaporate water contained in the three-dimensional object and thereafter immersed in liquid containing a humectant to replace the water in the three-dimensional object with the humectant in order for the obtained three-dimensional object to contain a greater amount of humectant around the surface.

Furthermore, if this replacement of water in a three-dimensional object with the humectant is repeated, the humectant can be impregnated into not only the surface but also the inside to a degree that the proportion of the humectant reaches around 90 percent by mass.

In the case of the method 2, the proportion of a humectant is preferably 10-90 percent by mass. If the proportion is less than 10 percent by mass, an obtained object is easily dried. If the proportion is greater than 90 percent, electric conductivity of a hygrogel deteriorates.

The hydrogel object of the present disclosure as an internal organ model has no particular limit and can reproduce every internal organ in a human body, including brain, heart, gullet, stomach, bladder, small intestine, large intestine, liver, kidney, spleen, pancreas, and womb.

In addition, the hydrogel object of the present disclosure as an internal organ model can truly reproduce inclusions such as vessels and malady, have textures and a bite of scalpel extremely close to those of internal organs, and can be dissected with a surgical knife. Therefore, for example, it is suitable as an internal organ model for doctors, trainee doctors, and medical students to practice procedures. Also, it can be used to check the bite of a manufactured surgical scalpel before shipment of the scalpel or a surgical operation.

FIG. 1 is a diagram illustrating a liver model as the internal organ model for use in procedures.

Livers are the largest internal organs located on the right side of the upper abdomen and below ribs. It weighs 1.2-1.5 kg in the case of an adult human. Livers change nutrition taken from food into a form a human body can utilize and control "metabolism" (store and supply), detox to detoxify harmful materials, and secretion of bile which helps decomposition and absorption of fats, etc.

As illustrated in FIG. 1, a liver 40 is fixed to anterior abdominal wall by a falciform ligament of a liver 43 and separated into a left lobe 45 and a right lobe 44 by the main separating plane (Cantlie line) linking a cholecyst 41 and an inferior vena cava 42.

Hepatectomy is an operation to cut out a part of the liver. Diseases to which hepatectomy is applied are, for example, cancer of liver (primary cancer of liver) in most cases, metastatic cancer of the liver, benign hepatic tumor, injury of the liver, etc.

Hepatectomy are classified into partial ablation, subsegmentectomy, segmental resection, lobectomy, extended lobectomy, and risegmentectomy depending on how to cut. These parts are not marked on an actual liver. Therefore, in operation, surgeons tie up portals or hepatic artery to block the nutrition therefor or infuse pigment into vessels to change the color thereof to recognize borders. Thereafter, the surgeon cuts the liver with various devices such as cautery knife, harmonic scalpel (ultrasonic vibration surgical instrument), CUSA (ultrasonic surgical aspirator), and MICROTAZE (microwave surgical instrument).

In such a case, the hydrogel object of the present disclosure as an internal organ model can be suitably used for operation simulations because the internal organ model can truly reproduce internal structures such as vessels and malady, has textures and bites by a knife extremely close to those of a target internal organ, and can be dissected by a surgical scalpel.

Forming Device

FIG. 2 is a diagram illustrating a forming device 10 to form the liver model illustrated in FIG. 1 as the internal organ model. The forming device 10 uses a head unit having inkjet heads arranged, jets material for a soft object from an object forming liquid jetting head unit 11 and material for a hard object from support object forming liquid jetting head units 12 and 13, and laminates the material for a soft object while curing the material for a soft object by adjacent ultraviolet ray irradiators 14 and 15.

That is, the material for a hard object is jetted from the inkjet head (the support object forming liquid jetting head units 12 and 13) and solidified to form a first support layer having a pool. Thereafter, the liquid material for a soft object formed of an active energy ray curable compound is jetted from the inkjet head (object forming liquid jetting head unit 11) to the pool of the first support layer. The liquid material is cured by irradiation with an active energy ray and thereafter smoothed by smoothing members 20 and 21 to form the first object layer.

Thereafter, melted material for a hard object is jetted on the first support layer and solidified to laminate a second support layer having a pool. The liquid material for a soft object formed of the active energy ray curable compound is jetted to the pool of the second support layer. The liquid material is irradiated with an active energy ray to form a second object layer on the first object layer. Thereafter, the second object layer is smoothed to manufacture a three-dimensional laminate object layer 19 to obtain a three-dimensional laminate object.

When the multi-head unit moves in the direction indicated by the arrow A, a support layer 18 and the three-dimensional laminate object layer 19 are formed on an object layer supporting substrate 16 basically using the support object forming liquid jetting head unit 13, the object forming liquid jetting head unit 11, and the ultraviolet ray irradiator 14. At the same time, the support layer 18 and the three-dimensional laminate object layer 19 are smoothed by the smoothing member 20 having a roller form. The support object forming liquid jetting head unit 12 and the ultraviolet ray irradiator 15 may be auxiliarily used.

When the smoothing member having a roller form is used and the roller is reversely rotated against the operation direction, smoothing performance ameliorates.

When the multi-head unit moves in the direction indicated by the arrow B, a support layer 18 and the three-dimensional laminate object layer 19 are formed on an object layer supporting substrate 16 basically using the support object forming liquid jetting head unit 13, the object forming liquid jetting head unit 11, and the ultraviolet ray irradiator 15. At the same time, the support layer 18 and the three-dimensional laminate object layer 19 are smoothed by the smoothing member 21 having a roller form. The support object forming liquid jetting head unit 13 and the ultraviolet ray irradiator 14 may be auxiliarily used.

Furthermore, to keep the gap between the object forming liquid jetting head unit 11, the support object forming liquid jetting head unit 12, the support object forming liquid jetting head unit 13, the support object forming liquid jetting head unit 13, and the ultraviolet ray irradiator 15, the three-dimensional laminate object layer 19, and the support layer 18, a stage 17 is lowered according to the number of lamination.

Discharging Stabilizing Device

When an inkjet head is used, nozzle drying during non-discharging is an issue to stable operation. Therefore, if an inkjet head does not continuously discharge liquid for a long period of time, 1. the distal end of a discharging hole is prevented from being dried by covering (capping) the discharging hole with at least a member covering the distal end of the head, 2. a film having a high viscosity or a dry film appearing due to drying of liquid inside around the discharging hole is ejected by suction, 3. the discharging hole or the vicinity thereof is wiped off, to keep the discharging state stable for a long period of time.

This is extremely suitable in a process of forming a laminate object requiring a long period of time (24 hours or longer), in particular when liquid including a solvent such as water having a low boiling point is used to form a soft material.

Capping Process and Defective Discharging Recovery Flow

In the capping process, when suction instruction is issued after liquid discharging, the head moves to and contact with a cap portion. After the head is brought into contact with the cap, a pump starts suctioning to eject liquid through discharging holes including the defective discharging portion. After the suctioning is complete, the head moves along a wiping member to complete the wiping process.

Thereafter, the head is moved to the discharging position to resume discharging in the case of defective discharging recovery flow. In addition, when finishing discharging and forming, the head moves again to the position where the head is brought into contact with the cap to complete the capping process.

Defective Discharging Recovery Timing

When manufacturing a large laminate object, liquid is continuously discharged for a long period of time so that it is preferable to periodically conduct the defective discharging recovery flow.

When to recover from defective discharging can be determined arbitrarily. However, it is preferable to regularly conduct the recovery for each continuous operation within two hours in terms of recovering property of defective discharging.

Having generally described preferred embodiments of this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

The present disclosure is described with reference to embodiments.

The laminate objects represented by internal organ models are described in Examples but the present invention is not limited thereto.

"Parts" represents parts by mass and "percent" represents percent by mass unless otherwise specified in the following description.

Deionized water evacuated for ten minutes is described as "pure water" in the following description.

Example I-1

Preparation of Hydrogel Liquid Precursor 2 parts of sodium peroxodisulfate (manufactured by Wako Pure Chemical Industries, Ltd.) was dissolved in 98 parts of pure water to prepare an aqueous solution as a liquid initiator.

While stirring 100 parts of pure water, 8 parts of synthesized hectorite (laponite XLG, manufactured by RockWood) having a composition of $[Mg_{5.34}Li_{0.66}Si_8O_8(OH)_4]Na^-_{0.66}$ as water swellable laminate mineral was slowly added to the pure water followed by stirring to prepare a liquid dispersion.

Next, 30 parts of N,N-dimethylacrylamide (manufactured by Wako Pure Chemical Industries, Ltd.) which had passed through an active alumina column to remove a polymerization inhibitor was added to the liquid dispersion as the polymerizable monomer.

Next, 0.3 parts of dodecyl sodium sulfate (manufactured by Wako Pure Chemical Industries, Ltd.) was admixed as a surfactant.

Thereafter, 60 parts of glycerin was admixed as a humectant.

Thereafter, 0.1 parts of tetramethyl ethylenediamine (manufactured by Wako Pure Chemical Industries, Ltd.) was added while cooling down the thus-obtained liquid mixture in an ice bath.

Thereafter, 5 parts of the liquid initiator was admixed and stirred, the resultant was evacuated for 10 minutes to obtain a uniform hydrogel liquid precursor.

Formation of Gel Object

The thus-obtained hydrogel liquid precursor was charged into the following mold, left undone at 25 degrees C. for 20 hours, and taken out of the mold to obtain a liver model I-1.

Manufacturing of Mold

A material jetting device (AGILISTA, manufactured by KEYENCE CORPORATION) was used to form a processed mold utilizing three-dimensional model data of a liver.

Manufacturing of Vessel Inclusion Model

Vessels are formed using the hydrogel liquid precursor and the material jetting device and colored to be recognizable. These vessels are solidified to part of the mold and thereafter, the hydrogel liquid precursor was charged into the model. Thereafter, when the gel object is taken out of the mold in the end, the vessel was caused to remain in the internal organ model as an inclusion. A liver model including the vessel was thus-manufactured.

Since the thus-obtained liver model has the vessel reproduced at the exact position in a transparent real organ, all of the five surgeons who had evaluated this model agreed that the model can be used before an operation to visually confirm the position where a surgical scalpel is put.

Manufacturing 2 of Vessel Inclusion Model

A mold specially made for vessels was manufactured in the same manner as in "Manufacturing of Mold".

A hydrogel liquid precursor was prepared in the same manner as in the manufacturing of the hydrogel liquid precursor except that 2 parts of a coloring material (MS Magenta VP, manufactured by Mitsui Chemicals, Inc.) was further added and 8 parts of the synthesized hectorite (laponite XLG, manufactured by Rockwood) was increased to 18 parts. The prepared hydrogel liquid precursor was poured into the mold specially made for the vessel to form a harder hydrogel. Thus, a colored vessel model was obtained.

The thus-obtained vessel model was fixed to part of the model of the internal organ model. The prepared hydrogel liquid precursor was poured into the mold and thereafter a post-gelation liver model was taken out.

The five surgeons evaluated the liver model and agreed that it was possible to suture the vessel.

Example I-2

Preparation of Hydrogel Liquid Precursor

A hydrogel liquid precursor was prepared in the same manner as in Example I-1.

Formation of Gel Object

The thus-obtained hydrogel liquid precursor was discharged by a material jetting device utilizing the three dimensional model data of a liver. The liquid discharged was cured to obtain a liver model I-2.

Example I-3

Preparation of Hydrogel Liquid Precursor

A uniform hydrogel liquid precursor was prepared in the same manner as in Example I-1 except that the content of glycerin was changed to 120 parts.

Incidentally, when glycerin was mixed, dispersibility of the water swellable laminate clay mineral deteriorated. As a consequence, the liquid was thickened and flowability thereof was degraded. Although it was possible to handle them, the liquid was thickened to a degree that the liquid was not dischargeable in the inkjet method.

Formation of Gel Object

The thus-obtained hydrogel liquid precursor was charged into the same mold as that used in Example I-1, left undone at 25 degrees C. for 20 hours, and taken out of the mold to obtain a liver model I-3.

Example I-4

Preparation of Hydrogel Liquid Precursor

A uniform hydrogel liquid precursor was prepared in the same manner as in Example I-1 except that the content of glycerin was changed to 25 parts.

Formation of Gel Object

The thus-obtained hydrogel liquid precursor was charged into the same mold as that used in Example I-1, left undone at 25 degrees C. for 20 hours, and taken out of the mold to obtain a liver model I-4.

Example I-5

Preparation of Hydrogel Liquid Precursor

A uniform hydrogel liquid precursor was prepared in the same manner as in Example I-1 except that 60 parts of ethylalcohol was used as a humectant instead of glycerin.

Formation of Gel Object

The thus-obtained hydrogel liquid precursor was charged into the same mold as that used in Example I-1, left undone at 25 degrees C. for 20 hours, and taken out of the mold to obtain a liver model I-5.

Example I-6

Preparation of Hydrogel Liquid Precursor

A uniform hydrogel liquid precursor was prepared in the same manner as in Example I-1 except that 60 parts of ethylene glycol was used as a humectant instead of glycerin.

Formation of Gel Object

The thus-obtained hydrogel liquid precursor was charged into the same mold as that used in Example I-1, left undone at 25 degrees C. for 20 hours, and taken out of the mold to obtain a liver model I-6.

Comparative Example I-1

Preparation of Hydrogel Liquid Precursor

As a polymerization initiator, an aqueous solution was prepared in which 2 parts of sodium peroxodisulfate (manufactured by Wako Pure Chemical Industries, Ltd.) was dissolved in 98 parts of pure water.

Thereafter, while stirring 195 parts of pure water, 8 parts of synthesized hectorite (laponite XLG, manufactured by RockWood) having a composition of $[Mg_{5.34}Li_{0.66}Si_8O_8(OH)_4]Na^-_{0.66}$ as the water swellable laminate clay mineral was added little by little to the pure water followed by stirring to prepare a liquid dispersion.

Next, 20 parts of N,N-dimethylacrylamide (manufactured by Wako Pure Chemical Industries, Ltd.) which had passed through an active alumina column to remove a polymerization inhibitor was added to the liquid dispersion as the polymerizable monomer.

Next, 0.2 parts of dodecyl sodium sulfate (manufactured by Wako Pure Chemical Industries, Ltd.) was admixed as a surfactant.

Thereafter, 15 parts of glycerin was admixed as a humectant.

Thereafter, 0.1 parts of tetramethyl ethylenediamine (manufactured by Wako Pure Chemical Industries, Ltd.) was added while cooling down the thus-obtained liquid mixture in an ice bath.

Thereafter, 5 parts of the aqueous solution as the polymerization liquid initiator was admixed and stirred, the resultant was evacuated for 10 minutes to obtain a uniform hydrogel liquid precursor.

Formation of Gel Object

The thus-obtained hydrogel liquid precursor was charged into the same mold as that used in Example I-1, left undone at 25 degrees C. for 20 hours, and taken out of the mold to obtain a liver model I-7 as the target gel object.

Comparative Example I-2

Preparation of Hydrogel Liquid Precursor

A hydrogel liquid precursor was prepared in the same manner as in Comparative Example 1.

Formation of Gel Object

The thus-obtained hydrogel liquid precursor was discharged by a material jetting device utilizing the three dimensional model data of a liver. The liquid discharged was cured to obtain a liver model I-8 as the target gel object.

Comparative Example I-3

Preparation of Hydrogel Liquid Precursor

As a liquid initiator, an aqueous solution was prepared in which 2 parts of sodium peroxodisulfate (manufactured by Wako Pure Chemical Industries, Ltd.) was dissolved in 98 parts of pure water.

A uniform hydrogel liquid precursor was prepared in the same manner as in Comparative Example 1 except that the content of the pure water in the liquid dispersion was changed to 100 parts, the content of N,N-dimethylacrylamide glycerin was changed to 30 parts, and the content of glycerin was changed to 150 parts.

However, when glycerin was mixed, the liquid was thickened and lost flowability. This is considered to be caused by degradation of dispersibility of the water swellable laminate clay mineral. Therefore, a gel object was not formed.

Comparative Example I-4

Preparation of Hydrogel Liquid Precursor

A uniform hydrogel liquid precursor was prepared in the same manner as in Comparative Example I-1 except that no glycerin (humectant) was added.

Formation of Gel Object

The thus-obtained hydrogel liquid precursor was charged into the same mold as that used in Example I-1, left undone at 25 degrees C. for 20 hours, and taken out of the mold to obtain a liver model I-9 as the target gel object.

Table 1 shows the contents of each component constituting the hydrogel liquid precursor in Examples I-1 to I-6 and Comparative Example I-1 to I-4.

TABLE 1

| Composition of hydrogel liquid precursor | | Example | | | | | |
|---|---|---|---|---|---|---|---|
| | | I-1 | I-2 | I-3 | I-4 | I-5 | I-6 |
| Liquid precursor | Pure water (parts) | 100 | 100 | 100 | 100 | 100 | 100 |
| | Laponite XLG (parts) | 8 | 8 | 8 | 8 | 8 | 8 |
| | Polymerizable monomer (N,N-dimethylacrylamide) (parts) | 30 | 30 | 30 | 30 | 30 | 30 |
| | Surfactant (dodecyl sodium sulfate) (parts) | 0.3 | 0.3 | 0.3 | 0.3 | 0.3 | 0.3 |
| | Polymerization catalyst (tetramethyldiamine) (parts) | 0.1 | 0.1 | 0.1 | 0.1 | 0.1 | 0.1 |
| Polymerization liquid initiator | Pure water 98 parts Peroxodisodium sulfate 2 parts | 5 | 5 | 5 | 5 | 5 | 5 |
| Humectant | Glycerin (parts) | 60 | 60 | 120 | 25 | | |
| | Ethylalcohol (parts) | | | | | 60 | |
| | Ethylene glycol (parts) | | | | | | 60 |
| | Proportion of humectant | 30% | 30% | 46% | 15% | 29% | 29% |

TABLE 1-continued

| Composition of hydrogel liquid precursor | | Comparative Example | | | |
|---|---|---|---|---|---|
| Forming method | | Pouring molding | Material jetting | Pouring molding | Pouring molding |
| Liver model No. | | I-1 | I-2 | I-3 | I-4 |
| Liquid precursor | Pure water (parts) | 195 | 195 | 100 | 195 |
| | Laponite XLG (parts) | 8 | 8 | 8 | 5 |
| | Polymerizable monomer (N,N-dimethylacrylamide) (parts) | 20 | 20 | 30 | 20 |
| | Surfactant (dodecyl sodium sulfate) (parts) | 0.2 | 0.2 | 0.3 | 0.2 |
| | Polymerization catalyst (tetramethyldiamine) (parts) | 0.1 | 0.1 | — | 0.1 |
| Polymerization liquid initiator | Pure water 98 parts Peroxodisodium sulfate 2 parts | 5 | 5 | — | 5 |
| Humectant | Glycerin (parts) | 15 | 15 | 150 | |
| | Ethylalcohol (parts) | | | | |
| | Ethylene glycol (parts) | | | | |
| Proportion of humectant | | 6% | 6% | 51% | 0% |
| Forming method | | Pouring molding | Inkjet stereolithography | — | Pouring molding |
| Liver model No. | | I-7 | I-8 | — | I-9 |

Evaluation

Evaluation on Drying Property

The liver model I-1 to the liver model I-9 manufactured in Examples I-1 to Examples I-6, Comparative Example I-1, Comparative Example I-2, and Comparative Example I-4 were left undone at 25 degrees C. and relative humidity of 50 percent for one week and the mass loss rate was evaluated.

Evaluation on Internal Organ Reproducibility

The five veteran surgeons were interviewed to evaluate elasticity and bites of surgical knives of the liver models manufactured in Examples I-1 to Examples I-6, Comparative Example I-1, Comparative Example I-2, and Comparative Example I-4.

TABLE 2

| | | Humectant | Proportion of humectant (percent by mass) | Mass loss rate after being left undone (percent by mass) | State after being left undone |
|---|---|---|---|---|---|
| Example I-1 | Liver model I-1 | Glycerin | 30 | 8.3 | No change recognized |
| Example I-2 | Liver model I-2 | Glycerin | 30 | 8.7 | No change recognized |
| Example I-3 | Liver model I-3 | Glycerin | 46 | 5.2 | No change recognized |
| Example I-4 | Liver model I-4 | Glycerin | 15 | 12.6 | No change recognized |
| Example I-5 | Liver model I-5 | Ethylene glycol | 29 | 9.8 | No change recognized |
| Example I-6 | Liver model I-6 | Ethylene glycol | 30 | 9.2 | No change recognized |
| Comparative Example I-1 | Liver model I-7 | Glycerin | 6 | 21.2 | Wet touch lost and contraction occurred due to drying |
| Comparative Example I-2 | Liver model I-8 | Glycerin | 6 | 24.6 | Wet touch lost and contraction occurred due to drying |
| Comparative Example I-3 | — | Glycerin | 51 | | Unable to form (not evaluated) |
| Comparative Example I-4 | Liver model I-9 | — | 0 | 48.7 | Wet touch lost and contraction occurred due to drying |

Evaluation Result on Drying Property

The liver model I-1 to the liver model 1-6 manufactured in Examples I-1 to Examples I-6 contained the humectant in an amount of 15-46 percent.

These liver models were left undone at 25 degrees C. and relative humidity of 50 percent for one week and the mass loss rate was 5.2-12.6 percent. It was confirmed that textures of the liver models were not changed by drying but remained the same in the general environment.

The liver model I-7 and the liver model I-8 of Comparative Example I-1 and Comparative Example I-2 contained the humectant in an amount of 6 percent.

These liver models were left undone at 25 degrees C. and relative humidity of 50 percent for one week and the mass loss rate due to drying was 21.2 percent and 24.6 percent. The wet touch of the liver models was slightly lost and contraction due to drying occurred.

The liver model I-9 of Comparative Example I-4 contained no humectant.

The mass loss rate of the liver model I-9 left undone at 25 degrees C. and relative humidity of 50 percent for one week was 48.7 percent. The wet touch of the liver model was lost and contraction due to drying occurred.

Evaluation Result on Reproducibility of Internal Organ

The five veteran surgeons were interviewed to evaluate the liver model I-1 to the liver model I-9 and all agreed that the liver model I-1 to the liver model I-6 in Example I-1 to Example I-6 were true to life about elasticity and bites of surgical knives.

Example II-1

Preparation of Hydrogel Liquid Precursor

Deionized water evacuated for ten minutes is described as "pure water" in the following.

2 parts of sodium peroxodisulfate (manufactured by Wako Pure Chemical Industries, Ltd.) was dissolved in 98 parts of pure water to prepare an aqueous solution as a liquid initiator.

Thereafter, while stirring 195 parts of pure water, 8 parts of synthesized hectorite (laponite XLG, manufactured by RockWood) having a composition of $[Mg_{5.34}Li_{0.66}Si_8O_8(OH)_4]Na^-_{0.66}$ as the water swellable laminate clay mineral was added little by little to the pure water followed by stirring to prepare a liquid dispersion.

Next, 20 parts of N,N-dimethylacrylamide (manufactured by Wako Pure Chemical Industries, Ltd.) which had passed through an active alumina column to remove a polymerization inhibitor was added to the liquid dispersion as the polymerizable monomer.

Next, 0.2 parts of dodecyl sodium sulfate (manufactured by Wako Pure Chemical Industries, Ltd.) was admixed as a surfactant.

Thereafter, 0.1 parts of tetramethyl ethylenediamine (manufactured by Wako Pure Chemical Industries, Ltd.) was added while cooling down the thus-obtained liquid mixture in an ice bath.

Thereafter, 5 parts of the liquid initiator was admixed and stirred, the resultant was evacuated for 10 minutes to obtain a uniform hydrogel liquid precursor.

Formation of Gel Object

The thus-obtained hydrogel liquid precursor was charged into the following mold, left undone at 25 degrees C. for 20 hours, and taken out of the mold to obtain a liver model as the target gel object.

Manufacturing of Mold

A material jetting device (AGILISTA, manufactured by KEYENCE CORPORATION) was used to form a processed mold utilizing three-dimensional model data of a liver.

Impregnation Treatment of Gel Object in Humectant

The thus-obtained liver model was immersed in an aqueous solution containing glycerin as a humectant in an amount of 50 percent by mass at 25 degrees for one hour. The liver model II-1 as the target gel object was obtained by taking out of the aqueous solution.

Example II-2

Preparation of Hydrogel Liquid Precursor

A hydrogel liquid precursor was prepared in the same manner as in Example II-1.

Formation of Gel Object

The thus-obtained hydrogel liquid precursor was discharged by a material jetting device utilizing the three dimensional model data of a liver. The liquid discharged was cured to obtain a liver model.

Impregnation Treatment of Gel Object in Humectant

The thus-obtained internal organ model was immersed in an aqueous solution containing glycerin as a humectant in an amount of 50 percent by mass at 25 degrees for one hour. The liver model II-2 as the target gel object was obtained by taking out of the aqueous solution.

Example II-3

Preparation of Hydrogel Liquid Precursor

A hydrogel liquid precursor was prepared in the same manner as in Comparative Example I-2.

Formation of Gel Object

A liver model was manufactured in the same manner as in Comparative Example I-2 using the thus-obtained hydrogel liquid precursor.

Impregnation Treatment of Gel Object in Humectant

The thus-obtained liver model was immersed in an aqueous solution containing glycerin as a humectant in an amount of 50 percent by mass at 25 degrees for one hour. The liver model II-3 as the target gel object was obtained by taking out of the aqueous solution.

Example II-4

Preparation of Hydrogel Liquid Precursor

A hydrogel liquid precursor was prepared in the same manner as in Example II-1.

Formation of Gel Object

A liver model was manufactured in the same manner as in Example II-1 using the thus-obtained hydrogel liquid precursor.

Dried Gel Object Immersed in Humectant

When the liver model II-4 was left undone at 50 degrees C. and a relative humidity of 20 percent for 7 days. The mass loss rate was 78 percent.

Thereafter, the thus-obtained internal organ model was impregnated in an aqueous solution containing glycerin as a humectant in an amount of 50 percent by mass at 25 degrees for one hour. Thereafter, the internal organ model was left undone at 50 degrees C. and a relative humidity of 20 percent for three days. The mass loss rate was 38 percent. Thereafter, the thus-obtained internal organ model was impregnated in an aqueous solution containing glycerin as a humectant in an amount of 50 percent by mass at 25 degrees for one hour. Furthermore, the internal organ model was left undone at 50 degrees C. and a relative humidity of 20 percent for three days. The mass loss rate was 15 percent. Next, the thus-obtained internal organ model was immersed in glycerin as a humectant at 25 degrees for six hours. The liver model II-4 as the target gel object was obtained by taking out of glycerin.

Example II-5

Preparation of Hydrogel Liquid Precursor
A hydrogel liquid precursor was prepared in the same manner as in Example II-1.
Formation of Gel Object
A liver model was manufactured in the same manner as in Example II-1 using the thus-obtained hydrogel liquid precursor.
Impregnation Treatment of Gel Object in Humectant
The thus-obtained internal organ model was immersed in an aqueous solution containing ethyl alcohol as a humectant in an amount of 50 percent by mass at 25 degrees for one hour. The liver model II-5 as the target gel object was obtained by taking out of the aqueous solution.

Example II-6

Preparation of Hydrogel Liquid Precursor
A hydrogel liquid precursor was prepared in the same manner as in Example II-1.
Formation of Gel Object
A liver model was manufactured in the same manner as in Example II-1 using the thus-obtained hydrogel liquid precursor.
Impregnation Treatment of Gel Object in Humectant
The thus-obtained internal organ model was immersed in an aqueous solution containing ethylene glycol as a humectant in an amount of 50 percent by mass at 25 degrees for one hour. The liver model II-6 as the target gel object was obtained by taking out of the aqueous solution.

Comparative Example II-1

Preparation of Hydrogel Liquid Precursor
A hydrogel liquid precursor was prepared in the same manner as in Example II-1.
Formation of Gel Object
The thus-obtained hydrogel liquid precursor was charged into the same mold as that used in Example II-1, left undone at 25 degrees C. for 20 hours, and taken out of the mold to obtain a liver model II-7.

Comparative Example II-2

Preparation of Hydrogel Liquid Precursor
A hydrogel liquid precursor was prepared in the same manner as in Comparative Example II-1.
Formation of Gel Object
The thus-obtained hydrogel liquid precursor was discharged by a material jetting device utilizing the three dimensional model data of a liver. The discharged liquid was cured to obtain a liver model II-8.

Table 3 shows the contents of each component constituting the hydrogel liquid precursor in Examples II-1 to II-6 and Comparative Example II-1 to II-2.

TABLE 3

| Composition of hydrogel liquid precursor | | Example | | | | | |
|---|---|---|---|---|---|---|---|
| | | II-1 | II-2 | II-3 | II-4 | II-5 | II-6 |
| Liquid precursor | Pure water (parts) | 195 | 195 | 195 | 195 | 195 | 195 |
| | Laponite XLG (parts) | 8 | 8 | 8 | 8 | 8 | 8 |
| | Polymerizable monomer (N,N-dimethylacrylamide) (parts) | 20 | 20 | 20 | 20 | 20 | 20 |
| | Surfactant (dodecyl sodium sulfate) (parts) | 0.2 | 0.2 | 0.2 | 0.2 | 0.2 | 0.2 |
| | Polymerization catalyst (tetramethyldiamine) (parts) | 0.1 | 0.1 | 0.1 | 0.1 | 0.1 | 0.1 |
| Polymerization liquid initiator | Pure water 98 parts Peroxodisodium sulfate 2 parts (parts) | 5 | 5 | 5 | 5 | 5 | 5 |
| Humectant | Glycerin (parts) | | | | 15 | | |
| | Ethylalcohol (parts) | | | | | | |
| | Ethylene glycol (parts) | | | | | | |
| | Forming method | Pouring molding | Material jetting | Pouring molding | Pouring molding | Pouring molding | Pouring molding |
| | Glycerin | 50% | 50% | 50% | 50% | | |
| | Ethylalcohol | | | | | 50% | |
| | Ethylene glycol | | | | | | 50% |
| | Proportion of humectant | 30% | 30% | 46% | 15% | 29% | 29% |
| | Liver model No. | II-1 | II-2 | II-3 | II-4 | II-5 | II-6 |

TABLE 3-continued

|  |  | Comparative Example | |
|---|---|---|---|
| Composition of hydrogel liquid precursor | | II-1 | II-2 |
| Liquid precursor | Pure water (parts) | 195 | 195 |
| | Laponite XLG (parts) | 8 | 8 |
| Polymerizable monomer (N,N-dimethylacrylamide) (parts) | | 20 | 20 |
| Surfactant (dodecyl sodium sulfate) (parts) | | 0.2 | 0.2 |
| Polymerization catalyst (tetramethyldiamine) (parts) | | 0.1 | 0.1 |
| Polymerization liquid initiator | Pure water 98 parts Peroxodisodium sulfate 2 parts (parts) | 5 | 5 |
| Humectant | Glycerin (parts) Ethylalcohol (parts) Ethylene glycol (parts) | | |
| | Forming method | Pouring molding | Material jetting |
| | Glycerin | 15% | 150% |
| | Ethylalcohol | | |
| | Ethylene glycol | | |
| | Proportion of humectant | 6% | 51% |
| | Liver model No. | II-7 | II-8 |

Evaluation

Content of Humectant

The content of the humectant in the liver model II-1 to the liver model II-8 manufactured in Examples II-1 to Example II-1 and Comparative Example II-1 and Comparative Example II-2 was measured by a thermogravimetric analyzer (Thermoplus TG8129, manufactured by Rigaku Corporation). The measuring method of the content of the humectant around the surface of the liver model is as follows.

A hydrogel having a size of 2 mm×2 mm is cut out from the surface of the liver model. This hydrogel is placed in a thermogravimetric analyzer to measure the thermogravimetric decrease rate around the boiling point of the humectant. Specifically, since glycerin having a boiling point of 290 degrees C. was used as the humectant in the present disclosure, the mass loss value of glycerin was measured in the temperature range of 250-300 degrees C. The content of the humectant was measured from the mass loss rate of glycerin as the mass of the 2 mm×2 mm hydrogel was determined to be 100 percent.

In addition, the content of the humectant inside the liver model was obtained by cutting out a hydrogel of 2 mm×2 mm at 50 mm inside from the surface of the liver model and measuring in the same manner as in the case where the humectant around the surface was measured as described above.

Evaluation on Drying Property

The liver model II-1 to the liver model II-8 manufactured in Examples II-1 to Examples 11-6, Comparative Example II-1 and Comparative Example II-2 were left undone at 25 degrees C. and relative humidity of 50 percent for one week and the mass loss rate was evaluated.

The results are shown in Table 4.

Evaluation on Internal Organ Reproducibility

The five veteran surgeons were interviewed to evaluate elasticity and bites of surgical knives of the liver models manufactured in Examples II-1 to Examples 11-6, Comparative Example II-1 and Comparative Example II-2.

TABLE 4

| | | Humectant | Proportion of humectant (percent by mass) | Mass loss rate after being left undone (percent by mass) | State after being left undone |
|---|---|---|---|---|---|
| Example II-1 | Liver model II-1 | Glycerin | 12 | 13.6 | No change recognized |
| Example II-2 | Liver model II-2 | Glycerin | 13 | 12.9 | No change recognized |
| Example II-3 | Liver model II-3 | Glycerin | 25 | 10.2 | No change recognized |
| Example II-4 | Liver model II-4 | Glycerin | 90 | 0.8 | No change recognized |
| Example II-5 | Liver model II-5 | Ethylene glycol | 30 | 9.8 | No change recognized |
| Example II-6 | Liver model II-6 | Ethylene glycol | 30 | 9.2 | No change recognized |
| Example II-1 | Liver model II-7 | Glycerin | 0 | 48.7 | Wet touch lost and contraction occurred due to drying |
| Example II-2 | Liver model II-8 | Glycerin | 0 | 45.2 | Wet touch lost and contraction occurred due to drying |

Evaluation on Drying Property

The liver models in Examples II-1 to Examples 11-6 contained the humectant in an amount of 12-90 percent.

These liver models were left undone at 25 degrees C. and relative humidity of 50 percent for one week and the mass loss rate was 0.8-13.6 percent. It was confirmed that textures of the liver models were not changed by drying but remained the same in the general environment.

The proportion of the humectant in the liver model II-7 in Comparative Example II-1 and the liver model II-8 in Comparative Example II-2 was 0 percent. The mass loss rate of the liver model II-7 and the liver model II-8 left undone at 25 degrees C. and relative humidity of 50 percent for one week was 48.7 percent and 45.2 percent, respectively. The wet touch of the liver model was slightly lost and contraction occurred due to drying.

Evaluation Result on Reproducibility of Internal Organ

The five veteran surgeons were interviewed to evaluate the liver model II-1 to the liver model II-6 of Examples and all agreed that the liver models were true to life about elasticity and bites of surgical knives.

Example III-1

Preparation of Hydrogel Liquid Precursor

Deionized water evacuated for ten minutes is described as "pure water" in the following.

2 parts of sodium peroxodisulfate (manufactured by Wako Pure Chemical Industries, Ltd.) was dissolved in 98 parts of pure water to prepare an aqueous solution as a liquid initiator.

Thereafter, while stirring 195 parts of pure water, 8 parts of synthesized hectorite (laponite XLG, manufactured by RockWood) having a composition of $[Mg_{5.34}Li_{0.66}Si_8O_8(OH)_4]Na^-_{0.66}$ as the water swellable laminate clay mineral was added little by little to the pure water followed by stirring to prepare a liquid dispersion.

Next, 20 parts of N,N-dimethylacrylamide (manufactured by Wako Pure Chemical Industries, Ltd.) which had passed through an active alumina column to remove a polymerization inhibitor was added to the liquid dispersion as the polymerizable monomer.

Next, 0.2 parts of dodecyl sodium sulfate (manufactured by Wako Pure Chemical Industries, Ltd.) was admixed as a surfactant.

Thereafter, 0.1 parts of tetramethyl ethylenediamine (manufactured by Wako Pure Chemical Industries, Ltd.) was added while cooling down the thus-obtained liquid mixture in an ice bath.

Thereafter, 5 parts of the aqueous solution as the polymerization liquid initiator was admixed and stirred, the resultant was evacuated for 10 minutes to obtain a uniform hydrogel liquid precursor.

Formation of Hygrogel Structure

The thus-obtained hydrogel liquid precursor was charged into the following mold, left undone still at 25 degrees C. for 20 hours, and taken out of the mold to obtain a hydrogel structure.

Manufacturing of Mold

A material jetting device (AGILISTA, manufactured by KEYENCE CORPORATION) was used to form a processed mold utilizing three-dimensional model data of a liver.

Film Forming

PLASTI COAT #100 (manufactured by DAIKYO CHEMICAL CO., LTD.) was applied to the surface of the obtained hygrogel structure by a dipping method to form a film having a thickness of 30 μm to obtain a liver model.

Example III-2

Another hydrogen structure was manufactured in the same manner as in Example III-1. A heat shrink film (D-955, manufactured by Sealed Air Japan G.K.) was used and heated by a heat gun to form a film having a thickness of 30 μm on the surface of the obtained hygrogel structure to obtain a liver model.

Example III-3

A liver model was manufactured in the same manner as in Example III-1 except that PLASTI COAT #100 was applied by a spraying method to the surface of the hydrogel structure to form a film thereon in Example III-1.

Example III-4

Vessels are formed using a material jetting device and colored to be recognizable when forming a liver model according to the method described in Example III-1. These vessels are fixed to part of the mold and thereafter, the same hydrogel liquid precursor as Example III-1 was charged into the model. Thereafter, when the gel object was taken out of the mold in the end, the vessel was caused to remain in the internal organ model as an inclusion. A liver model including the vessel was thus-manufactured.

Evaluation

Since the thus-obtained liver model has the vessel reproduced at the exact site in a transparent real organ, all of the five surgeons who had evaluated this model agreed that the model can be used prior to an operation to visually confirm the position where a surgical scalpel is put.

Example III-5

A mold specially made for the vessel in Example III-4 was manufactured in the same manner as described in Example III-1.

A hydrogel liquid precursor was prepared in the same manner as in the manufacturing of the hydrogel liquid precursor of Example III-1 except that 2 parts of a coloring material (MS Magenta VP, manufactured by Mitsui Chemicals, Inc.) was further added and 8 parts of the synthesized hectorite (laponite XLG, manufactured by Rockwood) was increased to 18 parts. The prepared hydrogel liquid precursor was poured into the mold specially made for the vessel to form a harder hydrogel. Thus, a colored vessel model was obtained.

The thus-obtained vessel model was fixed to part of the model of the internal organ model in the same manner as in Example III-4. The hydrogel liquid precursor prepared in the same manner as described in Example III-1 was poured into the mold and thereafter a post-gelation liver model was taken out.

Evaluation

The five surgeons evaluated the liver model and agreed that it was possible to suture the vessel.

Comparative Example III-1

A liver model was obtained in the same manner as in Example III-1 except that no film was formed on the surface of the hydrogel structure.

Evaluation

Mass loss rate and color change were evaluated for the liver models of Examples III-1 to III-3 and Comparative Example III-1 according to the following evaluation method.

Evaluation 1

The mass change of the liver model between before and after the model was left undone at 25 degrees C. and a relative humidity of 50 percent for one week.

Evaluation 2

After the liver model was stored in a room for one month, the three-dimensional object was cut to observe the color change of the inside thereof.

TABLE 5

|  | water vapor transmission rate (g/m² · d) | oxygen transmission rate (cc/m²/hr/atm) | difference of Young's modulus between a film and no film (MPa) | Mass loss rate (percent by mass) | Color change |
|---|---|---|---|---|---|
| Example III-1 | 35 | 6 | 0.4 | 2 | No change |
| Example III-2 | 5 | 250 | 1.1 | No change | No change |
| Example III-3 | 50 | 10 | 0.14 | 5 | No change |
| Comparative Example III-1 | — | — | — | 35 | Color changed due to occurrence of mold |

As seen in Table 5, the mass loss rate of the liver model of Examples III-1 to III-3 was small, somewhere between 0-5 percent, and no color change occurred.

To the contrary, the mass loss rate of the liver model of Comparative Example III-1 having no film formed was large and a color change was observed.

Example IV-1

Preparation of Hydrogel Liquid Precursor

Pure water was prepared by evacuating deionized water for 10 minutes.

2 parts of sodium peroxodisulfate (manufactured by Wako Pure Chemical Industries, Ltd.) was dissolved in 98 parts of pure water to prepare an aqueous solution as a liquid initiator.

While stirring 195 parts of pure water, 8 parts of synthesized hectorite (laponite XLG, manufactured by RockWood) having a composition of $[Mg_{5.34}Li_{0.66}Si_8O_8(OH)_4]Na^-_{0.66}$ as water swellable laminate mineral was slowly added to the pure water followed by stirring to prepare a liquid dispersion.

Next, 20 parts of N,N-dimethylacrylamide (manufactured by Wako Pure Chemical Industries, Ltd.) which had passed through an active alumina column to remove a polymerization inhibitor was added to the liquid dispersion as the polymerizable monomer.

Next, 0.2 parts of dodecyl sodium sulfate (manufactured by Wako Pure Chemical Industries, Ltd.) was admixed as a surfactant.

Thereafter, 30 parts of glycerin was admixed as a humectant.

Next, 0.2 parts of a preservative (Proxel GXL, containing 20 percent by mass of 1,2-benzoisothiazoline-3-one, manufactured by LONZA Japan) was admixed.

Thereafter, 0.1 parts of tetramethyl ethylenediamine (manufactured by Wako Pure Chemical Industries, Ltd.) was added while cooling down the thus-obtained liquid mixture in an ice bath.

After 5 parts of the liquid initiator was admixed and stirred, the resultant was evacuated for 10 minutes to obtain a uniform hydrogel liquid precursor.

Formation of Hygrogel

The thus-obtained hydrogel liquid precursor was charged into the following mold, left undone at 25 degrees C. for 20 hours, and taken out of the mold to obtain a liver model IV-1. The proportion of the Proxel GXL (S) (preservative) in the thus-obtained liver model IV-1 was 0.08 percent.

Manufacturing of Mold

A three-dimensional object manufacturing device (AGILISTA, manufactured by KEYENCE CORPORATION) was used to form a processed mold utilizing three-dimensional model data of a liver.

The decrease rate of light transmission rate in the visible light range, 80 percent compressive stress-strain, water amount, content of preservative, and mass loss rate were evaluated according to the following manner.

Decrease Rate of Light Transmission Rate in Visible Light Range

The light transmission rate in the visible light range of the thus-obtained liver model IV-1 before and after the model was left undone at 25 degrees C. and a relative humidity of 50 percent for one week was measured by a spectrophotometer (U3310 type, manufactured by Hitachi, Ltd.). The decrease rate of the light transmission in the visible light range obtained assigning into the following relation 1 was 14 percent. In that environment, propagation of germs such as fungus was not visually observed on the surface of the internal organ model.

Decrease rate of light transmission rate(percent)=
[(light transmission rate before being left undone)−(light transmission rate after being left undone)/(light transmission rate before being left undone)×100   Relation 1

80 Percent Compressive Stress-Strain

The thus-obtained hydrogel liquid precursor was poured into a mold, which was thereafter sealed by a lid of fused quartz and irradiated with an ultraviolet irradiator (SPOT CURE SP5-250DB, manufactured by USHIO INC.) in a light amount of 350 mJ/cm² to obtain a cube hydrogel of 10 mm×10 mm×10 mm.

The cube hydrogel was set in a universal tester (AG-1, manufactured by SHIMADZU CORPORATION) with a load cell of 1 kN and a compression jig for 1 kN. The stress to the compression applied to the load cell was recorded by a computer to plot the stress to the amount of displacement.

When the hydrogel modeling object was fractured, the compression stress at the time of the fracture was determined as the maximum value. The 80 percent compressive stress-strain was shown for the un-fractured hydrogel.

The 80 percent compressive stress-strain of the obtained liver model IV-1 was 0.73 mPa.

Water Amount

The water amount of the obtained liver model IV-1 was measured by a thermogravimetric analyzer (Thermo plus TG8120, manufactured by Rigaku Corporation).

A hydrogel having a size of 2 mm×2 mm was cut out from the surface of the liver model to measure the water amount of the surface of the liver model. This hydrogel was placed in a thermogravimetric analyzer to measure the thermogravimetric decrease rate around the boiling point of the hydrogel to calculate the water amount.

Content of Preservative

The content of the preservative in the obtained liver model IV-1 was measured by using a thermogravimetric analyzer (Thermo plus TG8120, manufactured by Rigaku Corporation).

A hydrogel having a size of 2 mm×2 mm was cut out from the surface of the liver model to measure the content of the preservative of the surface of the liver model. This hydrogel was placed in a thermogravimetric analyzer to measure the thermogravimetric decrease rate around the boiling point of the preservative. Specifically, Proxel GXL(S) was used as the preservative. Since Proxel GXL(S) contained 1,2-brnzoisothiazoline-3-one having a boiling point of 154-158 degrees C. in an amount of 20 percent by mass, the mass decrease of 1,2-benzoisothiazoline-3-one was measured in the temperature range of 120-160 degrees C. The proportion of the preservative was calculated from the mass decrease rate of 1,2-benzoisothiazoline-3-one when the mass of the 2 mm×2 mm hydrogel was determined to be 100 percent.

The content of the humectant inside of the liver model was obtained by cutting out a hydrogel of 2 mm×2 mm at 50 mm inside from the surface of the liver model and measuring in the same manner as in the case where the humectant around the surface was measured as described above.

Mass Loss Rate

The mass of the obtained liver model IV-1 before and after the liver model was left undone at 25 degrees C. and a relative humidity of 50 percent for one week was measured by an electronic scale (FX-500i, manufactured by A&D Company, Limited). The measuring results were assigned into the following relation 2 to obtain the mass loss rate.

Mass loss rate(percent)=[(mass before being left undone)−(mass after being left undone)]/(mass before being left undone)×100    Relation 2

The mass loss rate of the obtained liver model IV-1 was 10 percent and no change of the texture was confirmed According to the present disclosure, a laminate three-dimensional object having good storage stability is provided.

Also, according to the present disclosure, a three-dimensional object is provided which truly reproduces internal structures such as vessels and malady, has textures and bites by a knife extremely close to those of a target internal organ, and can be dissected by a surgical scalpel.

Having now fully described embodiments of the present invention, it will be apparent to one of ordinary skill in the art that many changes and modifications can be made thereto without departing from the spirit and scope of embodiments of the invention as set forth herein.

What is claimed is:

1. A hydrogel object comprising:
   a polymer; and
   water,
   wherein a rate of mass loss is not greater than 20 percent by mass when the hydrogel object is left undone for one week at 25 degrees C. and relative humidity of 50 percent, and
   wherein the hydrogel object is an internal organ model.

2. The hydrogel object according to claim 1, wherein a stress under 80 percent compression of the hydrogel object is 0.01-5.0 MPa.

3. The hydrogel object according to claim 1, further comprising a humectant in an amount of 10-90 percent by mass.

4. The hydrogel object according to claim 3, wherein the humectant includes glycerin.

5. The hydrogel object according to claim 1, further comprising a humectant, wherein density of the humectant increases from a center to a surface of the hydrogel object.

6. The hydrogel object according to claim 1, wherein the hydrogel object includes multiple areas where compression stress values are different.

7. The hydrogel object according to claim 1, wherein the rate of mass loss is not greater than 5 percent by mass.

8. The hydrogel object according to claim 1, wherein a surface of the hydrogel object has a film.

9. The hydrogel object according to claim 8, wherein water vapor transmission rate of the film is not greater than 500 g/m$^2$·d.

10. The hydrogel object according to claim 8, wherein oxygen transmission rate of the film is not greater than 100,000 cc/m$^2$/hr/atm.

11. The hydrogel object according to claim 8, wherein a difference of Young's modulus between the hydrogel object before the film is formed and the hydrogel object after the film is formed is not less than 0.01 MPa.

12. The hydrogel object according to claim 1, wherein a decrease rate of light transmission of the hydrogel object is not greater than 20 percent after the hydrogel object is left undone for one week at 25 degrees C. and relative humidity of 50 percent.

13. The hydrogel object according to claim 1, further comprising a mineral.

* * * * *